(12) United States Patent
Barry et al.

(10) Patent No.: US 7,380,654 B2
(45) Date of Patent: Jun. 3, 2008

(54) CONVEYOR TRACK DRIVE

(75) Inventors: Douglas Barry, Lincoln, NE (US);
Adrian Chan, Richmond Hill (CA);
Greg Rothman, Omaha, NE (US); Don R. Simms, Council Bluffs, IA (US);
Inna M. Zevakina, Omaha, NE (US)

(73) Assignee: Abbott Laboratories, Abbott Park, IL (US)

( * ) Notice: Subject to any disclaimer, the term of this patent is extended or adjusted under 35 U.S.C. 154(b) by 152 days.

(21) Appl. No.: 10/626,463

(22) Filed: Jul. 24, 2003

(65) Prior Publication Data

US 2005/0258018 A1    Nov. 24, 2005

Related U.S. Application Data

(60) Provisional application No. 60/398,893, filed on Jul. 26, 2002.

(51) Int. Cl.
*B65G 23/06* (2006.01)
(52) U.S. Cl. ..................... 198/834; 198/835
(58) Field of Classification Search ............... 198/834, 198/835, 836.1, 839, 853
See application file for complete search history.

(56) References Cited

U.S. PATENT DOCUMENTS

| 3,788,455 | A | * | 1/1974 | Dieckmann, Jr. | 198/831 |
| 4,086,855 | A | * | 5/1978 | Newbegin | 104/172.2 |
| 5,203,447 | A | * | 4/1993 | Ewert | 198/807 |
| 5,363,951 | A | * | 11/1994 | Mensch | 198/606 |
| 5,871,085 | A | * | 2/1999 | Yagi | 198/835 |
| 6,481,567 | B2 | * | 11/2002 | Layne et al. | 198/834 |
| 6,840,370 | B2 | * | 1/2005 | Haug et al. | 198/837 |

* cited by examiner

*Primary Examiner*—James R Bidwell
(74) *Attorney, Agent, or Firm*—David L. Weinstein

(57) ABSTRACT

A conveyor track drive includes a continuous loop conveyor for supporting and carrying a specimen container, with one portion of the conveyor extending through a drive housing. The conveyor includes a first segment extending through the housing, which then wraps around a portion of a drive sprocket, extends back upstream and around a portion of an idler sprocket and then includes a second segment transversely adjacent the first segment. A guide plate on the housing is positioned over the adjacent segments of the conveyor with a slot located to guide a specimen carrier from the first segment to the second segment. The specimen carrier then exits the housing on the second segment of the conveyor. A motor in the housing drives the drive sprocket to move the conveyor.

9 Claims, 5 Drawing Sheets

CONVEYOR TRACK DRIVE

CROSS-REFERENCES TO RELATED APPLICATIONS

This application claims the benefit of U.S. Provisional Application Ser. No. 60/398,893, filed Jul. 26, 2002.

STATEMENT AS TO RIGHTS TO INVENTIONS MADE UNDER FEDERALLY SPONSORED RESEARCH AND DEVELOPMENT (Not applicable)

BACKGROUND OF THE INVENTION (1) Field of the Invention

The present invention relates generally to track utilized in an automated clinical laboratory conveyor system, and more particularly to an improved drive mechanism for driving a dual track conveyor system.

(2) Background Information

Clinical laboratory testing has changed and improved remarkably over the past 80 years. Initially, tests or assays were performed manually and generally utilized large quantities of serum, blood or other materials and/or body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of physical specimen required to perform a particular test.

Instruments have been developed to increase the efficiency of testing procedures by reducing turnaround time and decreasing the volumes necessary to perform various assays. Robotic engineering has evolved to such a degree that various types of robots have been applied in the clinical laboratory setting.

The main focus of prior art laboratory automation relied on the implementation of conveyor systems to connect areas of a clinical laboratory. Known conveyor systems in the laboratory setting utilize separate conveyor segments to move specimens from a processing station to a specific laboratory work station. In order to obtain cost savings, one typical scenario called for specimens to be sorted manually and grouped together in a carrier rack to be conveyed to a specific location. In this way, a carrier would move a group of 5-20 specimens from the processing location to the specific work station for the performance of a single test on each of the specimens within the carrier rack.

With the development of new and improved automatic conveyor systems for laboratories and other environments, it is possible to select, track, and convey individual specimens throughout a laboratory for a variety of different testing, while maintaining a priority system for certain types of testing or special urgent requests for a time-specific response. These new automated conveyor systems are of various types and design, but the inventors herein have found that a dual conveyor system, using a pair of parallel conveyor tracks circulating throughout a laboratory, provides the greatest flexibility and versatility. The integration of various track devices with software directing the operation of the conveyor system and the various automated testing stations, has improved both the speed and capability of automated conveyor systems in recent years.

Track devices form the physical interface between the specimen samples in carriers being directed throughout the system, while the Laboratory Automation System (LAS) database provides direction for the system through its command and control features. The LAS and the various track devices work in combination to direct, manage and track all specimens throughout the system.

The inventors herein have found that the prior art drive mechanism for the conveyor track suffers several problems. One problem is in the limited length of "chain" or track that may be driven by a single drive motor. In order to provide a desired length for a track within a laboratory, ancillary motors may be required around the track to maintain the track at the desired speed.

An advantage of a dual track conveyor is the possibility of running the two tracks at different speeds. This permits a specimen to be moved to a "fast track" between various job sites, and to the slower track when awaiting the performance of a desired task. However, in the past, this was accomplished with separate drive mechanisms for each track, thereby increasing the cost of the system, as well as the cost to maintain the system.

BRIEF SUMMARY OF THE INVENTION

It is therefore a general object of the present invention to provide an improved drive mechanism for the track of an automated conveyor system.

A further object of the present invention is to provide a drive mechanism with dual outputs for running dual tracks at different speeds, simultaneously.

These and other objects will be apparent to those skilled in the art.

The conveyor track drive of the present invention includes a housing with a first continuous loop conveyor having a portion extending through the housing within a generally horizontal drive plane. The conveyor includes a first segment extending through the housing in the drive plane, then wraps around a portion of a drive sprocket, extends back upstream and around a portion of an idler sprocket and then includes a second segment transversely adjacent the first segment within the drive plane. A guide plate on the housing is positioned over the drive plane with a slot located to guide a specimen carrier from the first segment to the second segment at the point where the two segments are adjacent one another. A motor in the housing drives the drive sprocket to move the conveyor.

BRIEF DESCRIPTION OF THE SEVERAL VIEWS OF THE DRAWING

The preferred embodiment of the invention is illustrated in the accompanying drawings, in which similar or corresponding parts are identified with the same reference numeral throughout the several views, and in which.

DETAILED DESCRIPTION OF THE INVENTION

Figure 1:
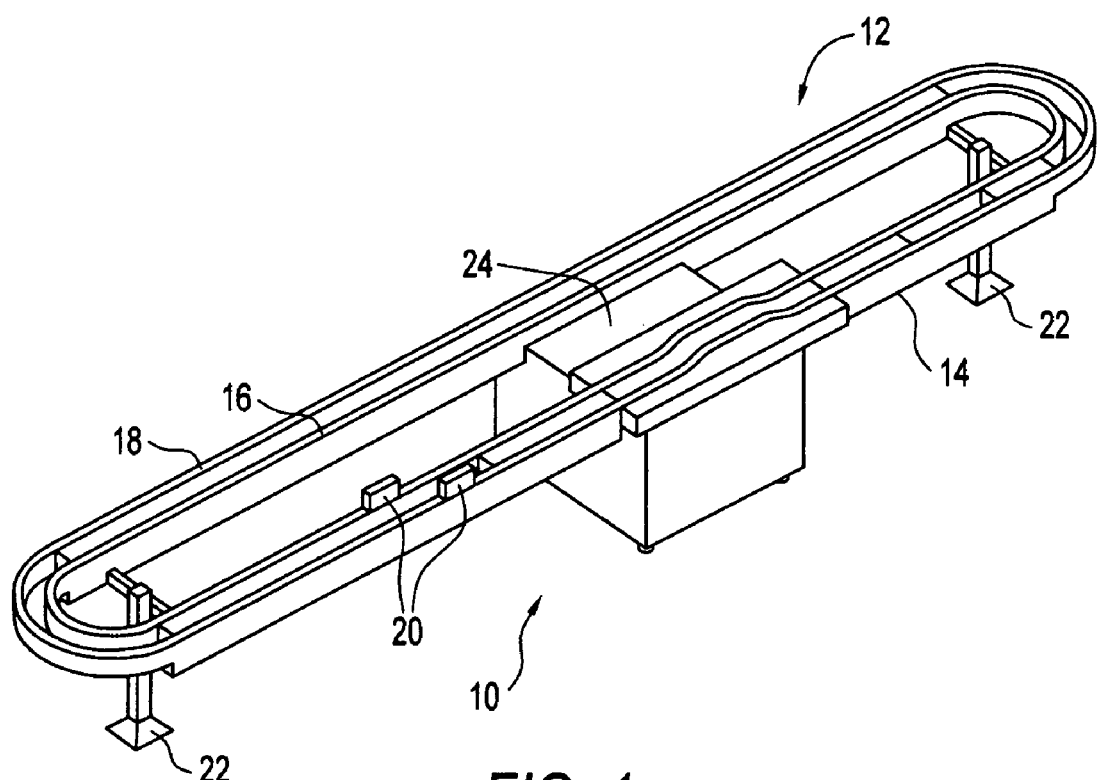
FIG. 1 is a perspective view of a conveyor drive mechanism of the present invention installed on a conveyor track.

Referring now to the drawings, in which similar or corresponding parts are identified with the same reference numeral, and more particularly to FIG. 1, the conveyor drive module of the present invention is designated generally at 10, and is shown installed on an automated conveyor transport system designated generally at 12.

Transport system 12 is a continuous loop, dual-lane conveyor having an integrated conveyor track 14 with an inside lane 16 and an outside lane 18 for transporting specimens within specimen carriers 20. Track 14 is supported above the ground by support frames 22 spaced along the track where needed, and by the housing 24 of drive mechanism 10.

Figure 2:
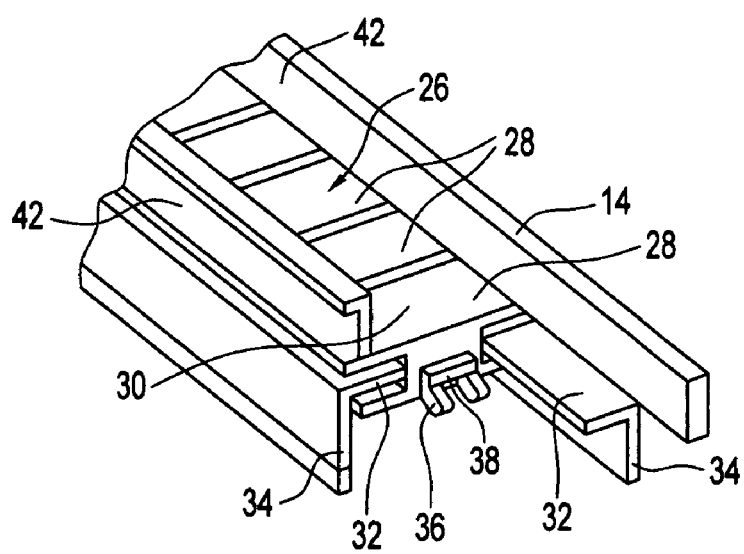
FIG. 2 is an enlarged cutaway perspective of a portion of the conveyor track.

Referring now to FIG. 2, one lane 18 of track 14 is cutaway to show the table top chain 26 in more detail. Table top chain 26 is known in the art, and includes a plurality of plates 28, each having a flat upper surface 30 (or "table top") and a generally "H"-shaped cross-section. A leg 32 of an elongated extrusion 34 projects within each of the notches of the "H" of the plates to guide the plates 28 as they are moved. Plates 28 are interconnected by links 36, which permit the plates 28 to pivot about the links 36 within a horizontal plane. The links 36 include a generally cylindrical rod 38, which is engaged by a sprocket 40 to drive the chain 26 and pull it along the guide extrusions 34. The upper surfaces 30 of plates 28 thereby form a flat planar surface that will transport specimen carriers 20 between a pair of guide rails 42.

Figure 3:
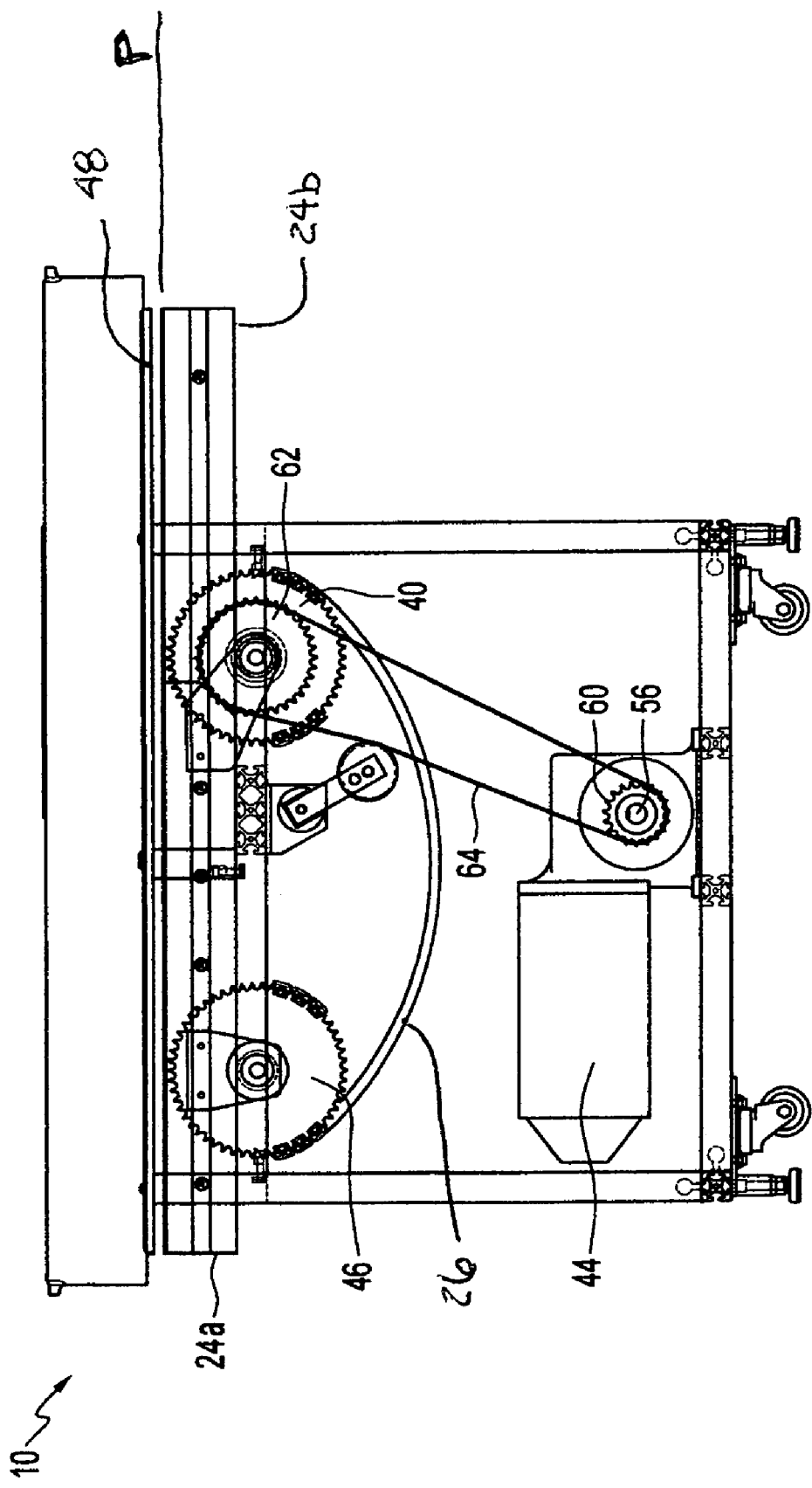
FIG. 3 is a side elevational view of the drive mechanism, with a cover removed for clarity.
Figure 4:
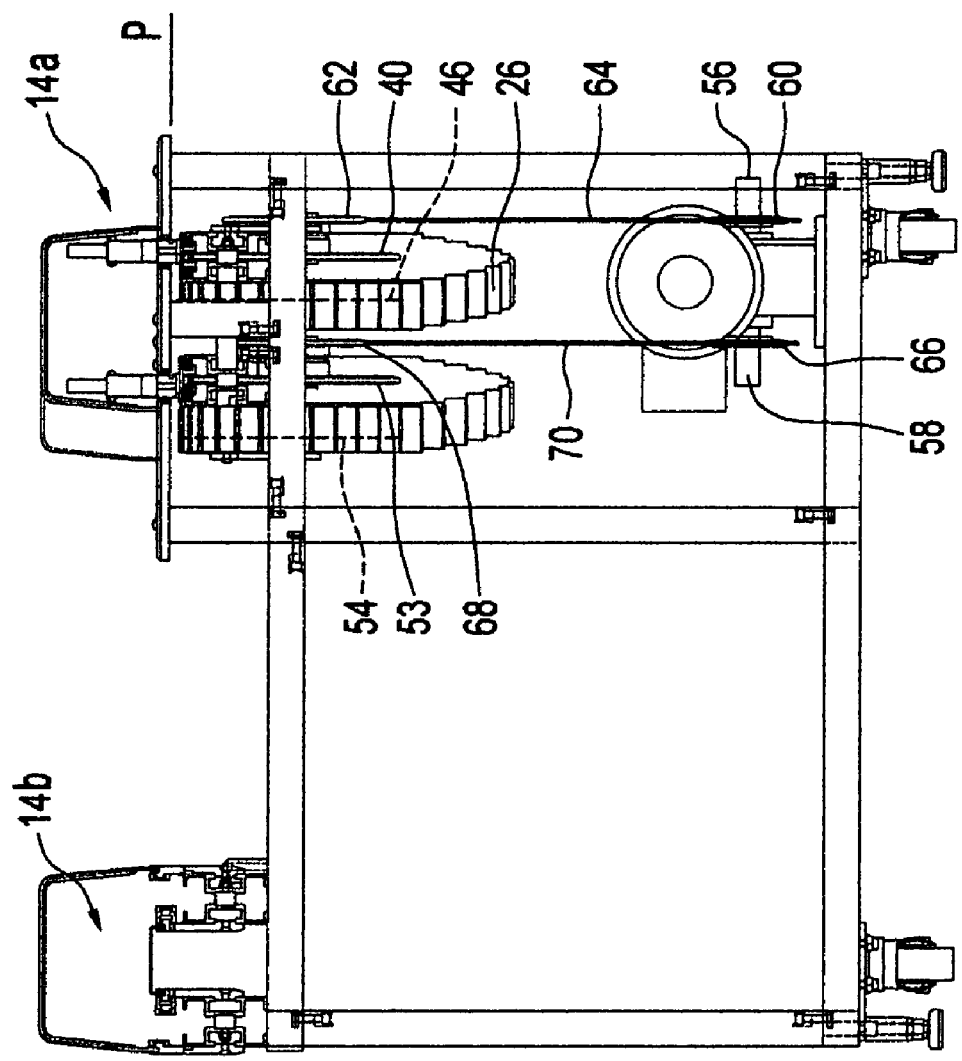
FIG. 4 is an end elevational view of the drive mechanism, showing the up-stream end of the device.
Figure 5:
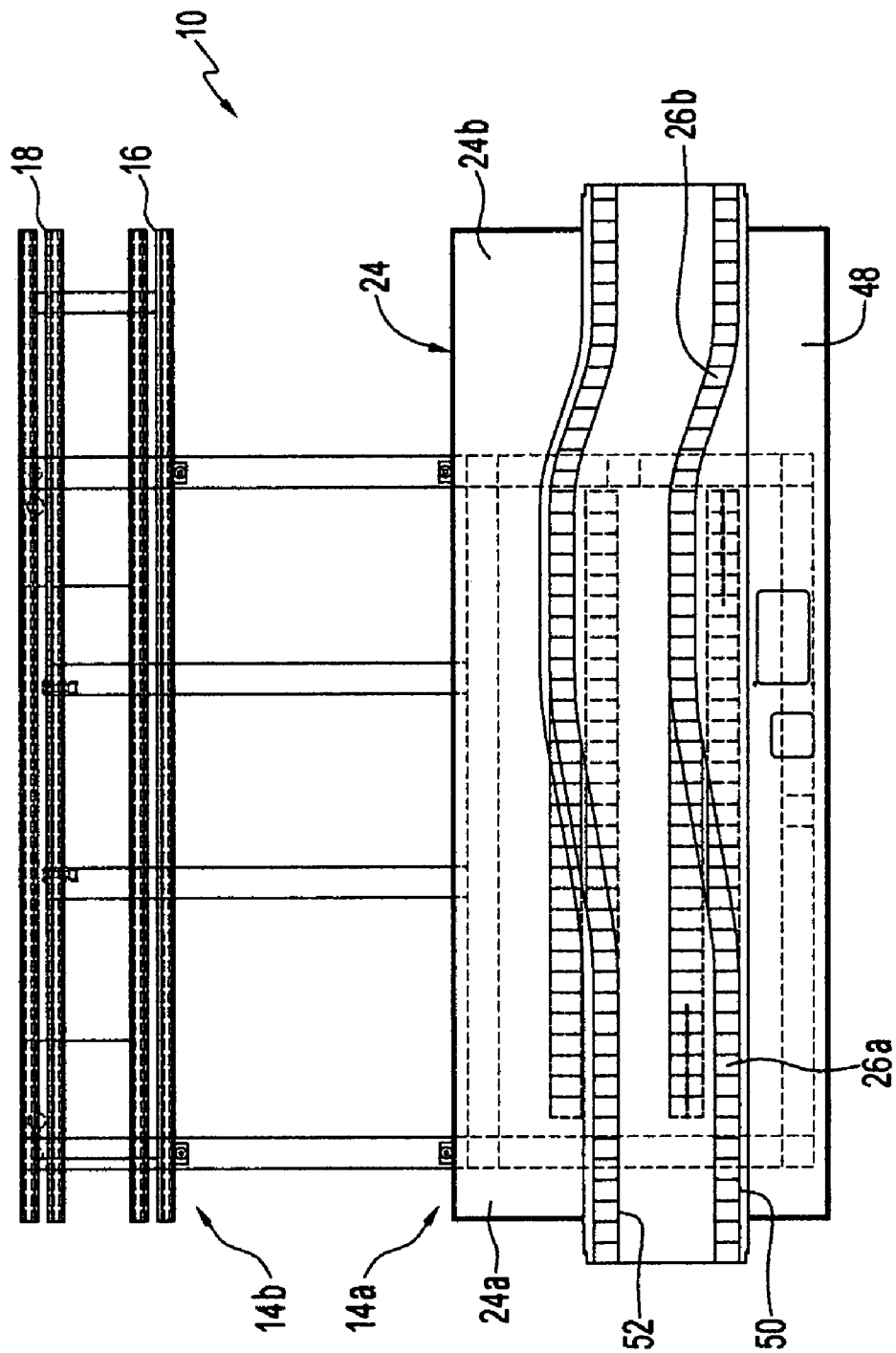
FIG. 5 is a top elevational view of the drive mechanism.

As shown in FIGS. 3 and 4, drive module 10 includes a housing 24 for supporting a drive motor 44 as well as two "runs" 14a and 14b of the dual-lane track 14 (also shown in FIG. 5). The chains 26 of the inside and outside lanes enter the module 10 at the upstream end 24a of housing 24 in a horizontal plane, hereinafter identified as the drive plane "P", formed by the plane of the upper surfaces of plates 28 of each chain 26.

Figure 6:
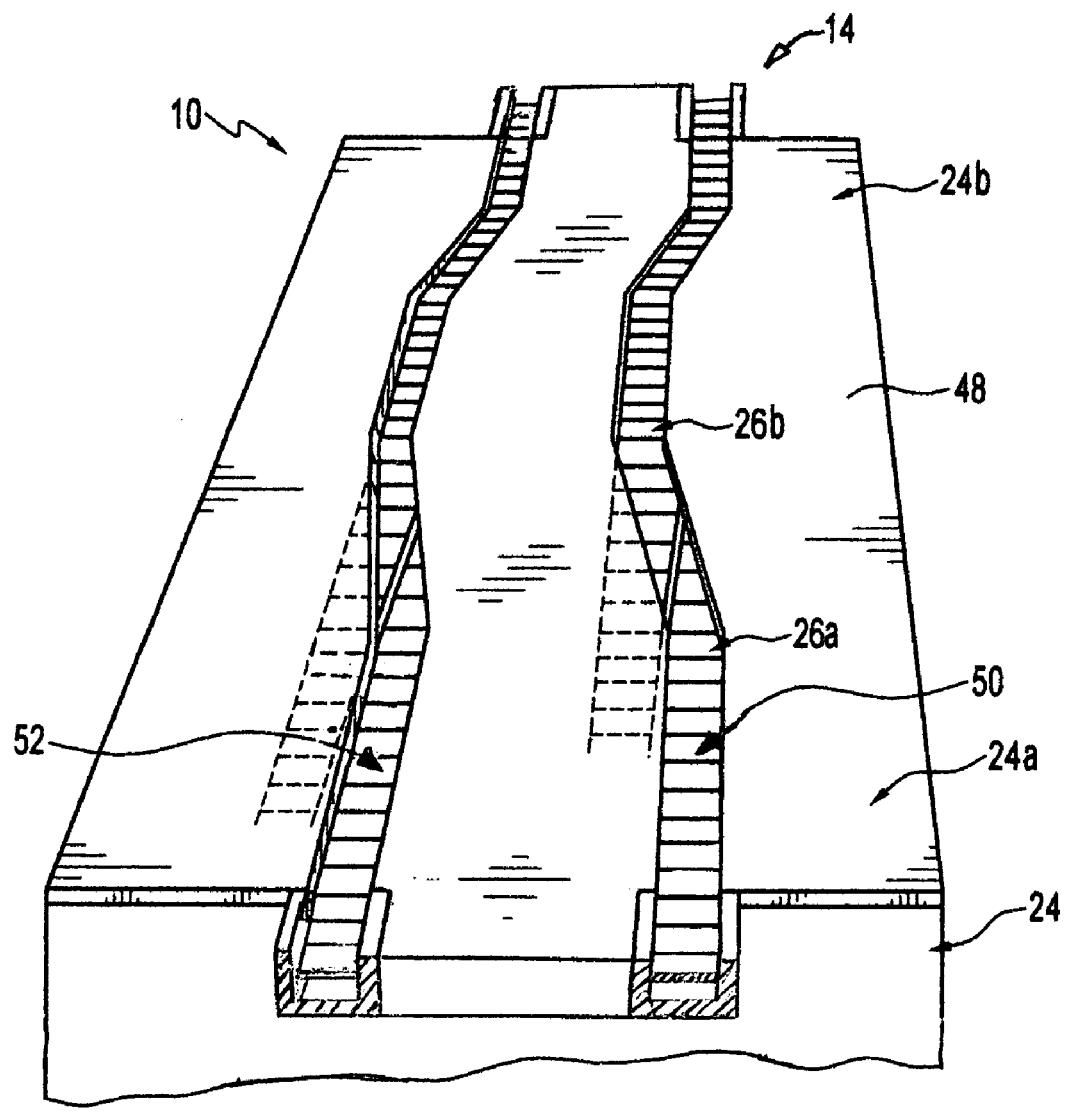
FIG. 6 is a perspective view of the guide plate of the invention, with the moving tracks shown in the guide slots.

Referring first to the outside lane 18 of track 14, and referring particularly to FIG. 6, it can be seen that chain 26 enters the drive module 10 at an upstream end 24a of housing 24 and proceeds in a straight path to the drive sprocket 40. Drive sprocket 40 engages the rods 38 of the links 36 (shown only in FIG. 2) to pull the chain 26, similar to prior art drives. However, the inventors herein have increased the performance and capabilities of the drive by altering the pathway of the chain 26 downward and around the drive sprocket 40 to thereby wrap around a portion of the sprocket 40. Chain 26 then proceeds under the sprocket 40 and back to the housing upstream end 24a (also shown in FIG. 3), where it is wrapped upwardly around an idler sprocket 46 and then proceeds in a downstream direction in the drive plane P (see FIG. 4), immediately adjacent the first segment 26a of chain 26 (as shown in FIG. 5).

As shown in FIGS. 5 and 6, after coming back to the drive plane P (shown only in FIG. 4) and proceeding downstream adjacent segment 26a, this second segment 26b of chain 26 continues to the downstream end 24b of housing 24 and continues into a section of track 14.

Referring now to FIG. 6, a carrier guide plate 48 is mounted on the upper end of housing 24 to guide specimen carriers 20 as they travel from the upstream end 24a to the downstream end 24b of the housing 24 on the drive plane P (shown only in FIG. 4). Guide plate 48 has two slots 50 and 52 formed therethrough, parallel to one another and extending from end to end. Slot 50 is aligned with the outside lane 18 of track 14 where the track connects with the upstream end 24a of housing 24, and continues to guide a specimen carrier 20 on the top of plates 28 of segment 26a of conveyor chain 26. About midway along segment 26a, slot 50 angles transversely and extends over segment 26b of chain 26. Slot 50 and segment 26b of chain 26 shift transversely back to the original line of travel of segment 26a immediately prior to exiting module 10 at the downstream end 24b of housing 24. Thus, the track 14 is aligned at the opposing ends of module 10.

Because the plates 28 of chain 26 reside within the same drive plane P (shown only in FIG. 4), specimen carriers 20 will easily slide transversely from chain segment 26a to segment 26b, without interruption of transport. While not described in detail herein, the inside lane 16 operates in the same fashion, with a first segment 26a of chain 26 wrapping around a drive sprocket 53, thence around an idler sprocket 54, and back into the same drive plane P adjacent the first chain segment 26a to form a second chain segment 26b which exits the drive module in alignment with the entry of the inside lane 16.

Referring again to FIGS. 3 and 4, drive motor 44 is preferably an AC frequency motor, with dual output shafts 56 and 58. Shaft 56 has a reduction gear 60 mounted thereon coplanar with a drive gear 62 mounted on the conveyor drive sprocket 40 for outside lane 18. A continuous loop chain 64 connects drive gear 62 with reduction gear 60 to drive the conveyor drive sprocket 40. Similarly, a reduction gear 66 on the second output shaft 58 is connected to a drive gear 68 on drive sprocket 54 by a continuous loop chain 70 to drive the chain 26 of the inside lane 16.

Because dual output drive shafts 56 and 58 are used, the chains 26 for the inside and outside lanes 16 and 18 may be operated at different speeds if desired. The use of the wraparound drive increases the pulling force of the drive motor, eliminating any need for additional drive motors for either of the two tracks of the dual-lane conveyor.

Whereas the invention has been shown and described in connection with the preferred embodiment thereof, many modifications, substitutions and additions may be made which are within the intended broad scope of the appended claims.

What is claimed is:

1. A conveyor track drive, comprising:
a housing having an upper end, a forward upstream end, a rearward downstream end, and opposing transverse sides;
a continuous loop track with a first continuous loop conveyor thereon, said first conveyor operably mounted on said housing with a first segment oriented in a generally horizontal drive plane, and a second segment coplanar with the first segment;
said first and second segments extending downstream in said drive plane, with a portion of each segment parallel and transversely adjacent one another;
a guide on said housing upper end, located above the drive plane, with first guide members oriented to direct an object on the conveyor first segment to the conveyor second segment at the parallel portion of the segments;
a drive sprocket operably mounted on the housing and in engagement with a downstream end of the first conveyor first segment to move the conveyor and the track and thereby transport objects on the conveyor;
an idler sprocket operably mounted on the housing in engagement with an upstream end of the second segment;

said first conveyor extending from the downstream end of the first segment, around a portion of the drive sprocket and thence around a portion of the idler sprocket to the upstream end of the second segment, to thereby form a continuous loop; and a selectively operable motor on the housing in engagement with the drive sprocket for selectively driving the drive sprocket.

2. The conveyor track drive of claim 1, wherein said first conveyor is a table top chain conveyor having a plurality of plates interconnected with links, upper surfaces of the plates forming the drive plane, and the drive and idler sprockets engaging the links.

3. The conveyor track drive of claim 1, wherein said guide is a guide plate extending from the upstream end to the downstream end of the housing, said guide plate including a first slot formed therethrough and extending from the upstream end to the downstream end, said guide members formed by the sides of said first slot.

4. The conveyor track drive of claim 1, wherein said motor includes a first output shaft with a reduction gear thereon, wherein said drive sprocket includes a drive gear for driving the sprocket, and further comprising a chain engaging the reduction gear with the drive gear to thereby drive the sprocket and move the first conveyor when the motor is operating to rotate the first output shaft.

5. The conveyor track drive of claim 1, further comprising:
   a second continuous loop conveyor on said track, generally parallel to the first conveyor, said second conveyor operably mounted on said housing with a first segment oriented in said drive plane, and a second segment coplanar with the first segment;
   said second conveyor first and second segments extending downstream in said drive plane, with a portion of each segment parallel and transversely adjacent one another;
   said guide including second guide members oriented to direct an object on the second conveyor first segment to the second conveyor second segment at the parallel portion of the segments;
   a second drive sprocket operably mounted on the housing and in engagement with a downstream end of the second conveyor first segment to move the conveyor in the track and thereby transport objects on the conveyor;
   a second idler sprocket operably mounted on the housing in engagement with an upstream end of the second conveyor second segment;
   said second conveyor extending from the downstream end of the second conveyor first segment, around a portion of the second drive sprocket and thence around a portion of the second idler sprocket to the upstream end of the second conveyor second segment, to thereby form a continuous loop; and
   said motor in engagement with the second drive sprocket for selectively driving the second drive sprocket.

6. The conveyor track drive of claim 5, wherein said conveyors are table top chain conveyors having a plurality of plates interconnected with links, upper surfaces of the plates forming the drive plane, and the drive and idler sprockets engaging the links of the associated chains.

7. The conveyor track drive of claim 5, wherein said guide is a guide plate extending from the upstream end to the downstream end of the housing, said guide plate including a pair of first and second slots formed therethrough and extending from the upstream end to the downstream end, said first guide members formed by the sides of said first slot and said second guide members formed by the sides of the second slot.

8. The conveyor track drive of claim 5:
   wherein said motor includes a first output shaft with a first reduction gear thereon and a second output shaft with a second reduction gear thereon;
   wherein said first drive sprocket includes a first drive gear for driving the first sprocket;
   wherein said second drive sprocket includes a second drive gear for driving the second sprocket;
   further comprising a first chain engaging the first reduction gear with the first, drive gear to thereby drive the first sprocket and move the first conveyor, and
   further comprising a second chain engaging the second reduction gear with the second drive gear to thereby drive the second sprocket and move the second conveyor.

9. The conveyor track drive of claim 8, wherein said first and second reduction gears are different sizes, such that said first and second conveyors move at different speeds.

* * * * *